(12) United States Patent
Owczarz et al.

(10) Patent No.: US 7,397,555 B2
(45) Date of Patent: Jul. 8, 2008

(54) SYSTEM, METHOD AND APPARATUS FOR IN-SITU SUBSTRATE INSPECTION

(75) Inventors: Aleksander Owczarz, San Jose, CA (US); Jaroslaw W. Winniczek, Daly City, CA (US); Luai Nasser, Union City, CA (US); Alan Schoepp, Ben Lomond, CA (US); Fred C. Redeker, Alameda, CA (US); Erik Edelberg, Castro Valley, CA (US)

(73) Assignee: Lam Research Corporation, Fremont, CA (US)

( * ) Notice: Subject to any disclaimer, the term of this patent is extended or adjusted under 35 U.S.C. 154(b) by 168 days.

(21) Appl. No.: 11/016,022

(22) Filed: Dec. 17, 2004

(65) Prior Publication Data

US 2006/0139450 A1    Jun. 29, 2006

(51) Int. Cl.
 *G01N 21/00* (2006.01)
(52) U.S. Cl. .................................. 356/237.3; 356/237.4
(58) Field of Classification Search ... 356/237.1–237.5, 356/445, 239.1–239.4
See application file for complete search history.

(56) References Cited

U.S. PATENT DOCUMENTS

| 5,581,348 | A | * | 12/1996 | Miura et al. ............. 356/237.2 |
| 5,864,394 | A |   | 1/1999  | Jordan, III et al. |
| 7,106,433 | B2 | * | 9/2006 | Hasan ...................... 356/237.4 |
| 7,177,019 | B2 | * | 2/2007 | Stanke et al. ............. 356/237.2 |
| 2004/0012775 | A1 | * | 1/2004 | Kinney et al. ............ 356/237.2 |
| 2004/0021856 | A1 | * | 2/2004 | Nishiyama et al. ....... 356/237.2 |
| 2006/0250612 | A1 | * | 11/2006 | Meeks ..................... 356/237.2 |

OTHER PUBLICATIONS

PCT International Search Report—PCT/US05/42918, Feb. 14, 2007.

* cited by examiner

*Primary Examiner*—Hoa Q Pham
(74) *Attorney, Agent, or Firm*—Martine Penilla & Gencarella, LLP

(57) ABSTRACT

A system for inspecting a substrate includes a camera and a light source. The camera is oriented toward a field of view. The field of view encompasses at least a first portion of a first surface of the substrate. The light source is oriented toward the field of view at a first angle $\beta$ relative to the first surface of the substrate. A method for inspecting a substrate is also included.

10 Claims, 9 Drawing Sheets

SYSTEM, METHOD AND APPARATUS FOR IN-SITU SUBSTRATE INSPECTION

BACKGROUND OF THE INVENTION

1. Field of the Invention

The present invention relates generally to substrate inspection and more particularly, to systems and methods for inspecting substrates.

2. Description of the Related Art

The semiconductor chip fabrication process requires numerous operations and sub-processes. Examples of such a fabrication operations include etching, chemical mechanical polishing (CMP), deposition, rinsing, drying and other operations. Each of the manufacturing operations must be monitored to make sure that the operation is completed accurately, repeatably and in a timely manner.

Many types of manufacturing processes (e.g., etch, rinse, dry, deposition) must also have some sort of subsystem or sub-process capable of monitoring the progress of the respective manufacturing process. This is increasingly important as process control requirements become ever more stringent as device feature sizes become ever smaller and as the level of integration increases. Typically, the monitoring system or sub-process is separate from the manufacturing process. By way of example, in a wet chemical etch manufacturing process, the wet etch process is typically interrupted and the progress is evaluated as follows. The etch process is applied to the semiconductor substrate for an initial period. The semiconductor substrate is then rinsed, dried and removed from the etch process tool to be evaluated using metrology from an appropriate subsystem or sub-process to determine if the wet etch process has reached the desired goal. If the etch process has reached the desired goal (i.e., if the etch process has etched away the desired material) then a subsequent process (es) (e.g., clean, rinse, dry) is applied to the semiconductor substrate.

Alternatively, if the wet etch process has not attained the desired goal (i.e., if the etch process has not removed all of the desired material) then the etch process is applied to the semiconductor substrate again in a rework process. After one or more iterations of the rework process, the wet etch process will remove the desired material from the semiconductor substrate. In the case of a batch processing system, a single semiconductor substrate may be used to verify the rework process required (e.g., to correct process time) before reworking the entire batch of substrates. In the case of a single semiconductor substrate processing system, a similar method could be used before committing an entire lot of substrates for rework wet etch processing.

Another examples include cleaning and rinsing processes that use fluids (i.e., wet cleaning processes). The wet cleaning processes can leave fluid droplets on the surface being cleaned. The wet cleaning process can also leave particle contaminants on the surface being cleaned. Such droplets and particles can interfere with subsequent processes. As described above, typical process monitoring is conducted in a separate inspection system. This separate inspection system requires additional handling and processing that negatively impacts throughput and increases the possibility for handling errors and damage.

In view of the foregoing, what is needed is an in-situ system and method for examining a surface to identify fluid droplets and particles on the surface after a wet cleaning process.

SUMMARY OF THE INVENTION

Broadly speaking, the present invention fills these needs by providing an in-situ system and method for examining a surface to identify fluid droplets and particles on the surface after a wet cleaning process. It should be appreciated that the present invention can be implemented in numerous ways, including as a process, an apparatus, a system, computer readable media, or a device. Several inventive embodiments of the present invention are described below.

One embodiment provides a system for inspecting a substrate includes a camera and a light source. The camera is oriented toward a field of view. The field of view encompasses at least a first portion of a first surface of the substrate. The light source is oriented toward the field of view at a first angle $\beta$ relative to the first surface of the substrate.

The system for inspecting the substrate is included in a process chamber for applying a manufacturing process to the substrate. The manufacturing process is supported by a dynamic liquid meniscus. The dynamic liquid meniscus is supported by a proximity head.

The light source is oriented toward the field of view at a second angle $\delta$ relative to a centerline of the camera. The light source includes at least one of a group consisting of an light emitting diode (LED) or a laser. The light source can include a red LED. The light source has a first intensity. The light source has a viewing angle of less than about 30 degrees. The light source can have a viewing angle of between about 15 degrees and less than about 8 degrees. The camera can be oriented toward the field of view at a third angle $\alpha$ relative to the first surface of the substrate.

The system can also include a controller coupled to the system for inspecting the substrate. The controller includes a recipe and an indicator.

Another embodiment provides a system for inspecting a substrate. The system including a first camera oriented toward a first field of view. The first field of view encompasses at least a first portion of a first surface of the substrate. A first light source oriented toward the first field of view at a first angle $\beta$ relative to the first surface of the substrate is also included. A second camera oriented toward a second field of view. The second field of view encompasses at least a second portion of a second surface of the substrate and a second light source oriented toward the second field of view at a second angle $\beta'$ relative to the second surface of the substrate are also included.

Yet another embodiment provides a method for inspecting a substrate. The method including recording a baseline dark field, directing a light source toward a field of view to be examined and receiving the field of view in a camera. The received field of view is compared to the baseline dark field. At least one of a droplet, a particle or a surface obstruction (DPO) can be detected within the received field and outputting a test result.

The method can also include placing the substrate within a process chamber, applying a manufacturing process to the substrate and inspecting the substrate in-situ within the manufacturing process. The manufacturing process is supported by a dynamic liquid meniscus. Outputting a test result can include stopping the manufacturing process.

The method can also include determining if the DPO can be corrected by the manufacturing process and if the DPO can be corrected by the manufacturing process then applying the manufacturing process to the substrate.

Detecting the at least one DPO can include comparing a first pixel in the dark field with a corresponding second pixel in the received field of view. Alternatively, detecting the at least one DPO can include comparing the first pixel in the dark field with the corresponding second pixel in the received field of view and wherein the DPO is detected if the second pixel has an intensity greater than the first pixel.

Other aspects and advantages of the invention will become apparent from the following detailed description, taken in conjunction with the accompanying drawings, illustrating by way of example the principles of the invention.

BRIEF DESCRIPTION OF THE DRAWINGS

The present invention will be readily understood by the following detailed description in conjunction with the accompanying drawings.

DETAILED DESCRIPTION OF THE EXEMPLARY EMBODIMENTS

Several exemplary embodiments for system and method for examining an in-situ surface to identify fluid droplets and particles on the surface after a wet cleaning process will now be described. It will be apparent to those skilled in the art that the present invention may be practiced without some or all of the specific details set forth herein.

Substrate inspection immediately following wet cleaning processes in a wet cleaning process chamber can confirm proper performance of the wet cleaning process chamber. By way of example, an in-situ substrate inspection occurring within the wet cleaning process chamber can confirm proper hardware (i.e., wet cleaning process chamber) performance and/or wet cleaning process performance. By way of example, the presence of droplets, particles or surface obstructions (i.e., DPO) can indicate hardware and/or process failure. Such failure must be identified immediately to ensure proper processing of subsequent substrates.

One embodiment uses an automated optical inspection of the surface being processed to detect DPO. The surface can be illuminated by a light source such that it is a dark field relative to a field of view of a camera and any DPOs that may be present are highlighted. The camera directed toward the surface can monitor the surface. A controller coupled to an output of the camera can identify any highlighted DPOs. The size and location of the DPOs can also be identified. By way of example, the size of a DPO can be correlated to an intensity of the DPO. Similarly, a location of a DPO can be correlated by a known location of a field of view of the camera relative to the surface.

Another embodiment can include a second camera and a second light source that can examine another surface. By way of example, the first camera and the first light source can be used to inspect a front surface of a semiconductor wafer while the second camera and the second light source can be used to inspect a back-side surface that is opposite from the front surface of the semiconductor wafer.

Figure 1A:
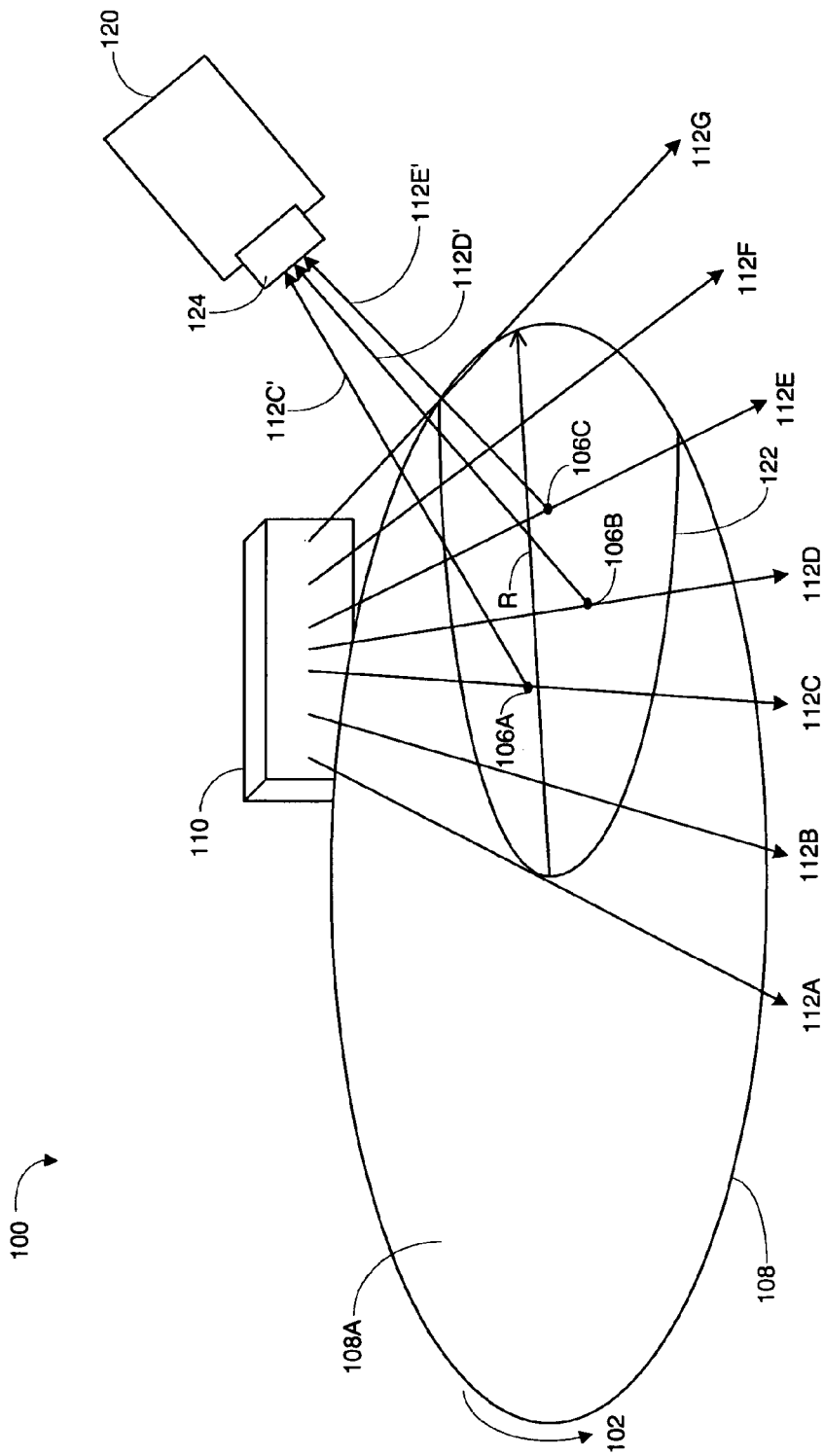
FIG. 1A is a block diagram of an in-situ optical inspection system, in accordance with one embodiment of the present invention

FIG. 1A is a block diagram of an in-situ optical inspection system 100, in accordance with one embodiment of the present invention. The in-situ optical inspection system 100 includes a light source 110 and a camera 120. Light 112A-112G emitted from the light source is shown across a front surface 108A of a wafer 108. As light 112C, 112D and 112E strikes a DPOs 106A, 106B and 106C, the corresponding reflected light 112C', 112D' and 112E' is reflected toward the camera 120. The wafer 108 can be rotated (e.g., in direction 102) so that the entire front surface 108A of the wafer 108 passes through the field of view 122 of the camera 120. In this manner, the camera 120 can inspect the entire front surface 108A of the wafer 108.

The wafer 108 can be supported by any of the well-known support methods and systems known in the art. By way of example, the wafer 108 can be supported on a platen or electrostatic chuck or a mechanical chuck from the back-side surface (i.e., the surface opposite from the front surface 108A) or the edges or any other manner of holding the wafer for processing. Alternatively, the wafer 108 can be supported by the edge of the wafer by two or more edge rollers or by finger-type robot end effectors.

In one embodiment, a size of a detected DPOs 106A, 106B and 106C is function of intensity or brightness of the reflected/diffracted light 112C', 112D' and 112E', respectively. The intensity of the reflected/diffracted light 112C', 112D' and 112E' can be calibrated so that a given intensity can accurately approximate a size. The light source 110 can also be strobed (i.e., flashed) so as to provide a substantially stopped view of a moving wafer 108. Similarly a shutter speed and aperture of the camera 120 can be selected to provide a more accurate detection of the DPOs. By way of example, if DPO 106B was a 2.0 mm water droplet, then the reflected/diffracted light 112D' would have a first intensity. Similarly, if DPO 106A were a 1.0 mm water droplet then the reflected/diffracted light 112C' would have a second intensity. The second intensity would likely be less than the first intensity as the DPO 106B is larger than DPO 106A. DPOs 106A, 106B and 106C can have sizes from less than about 1.0 mm to any larger size.

Figure 1B:
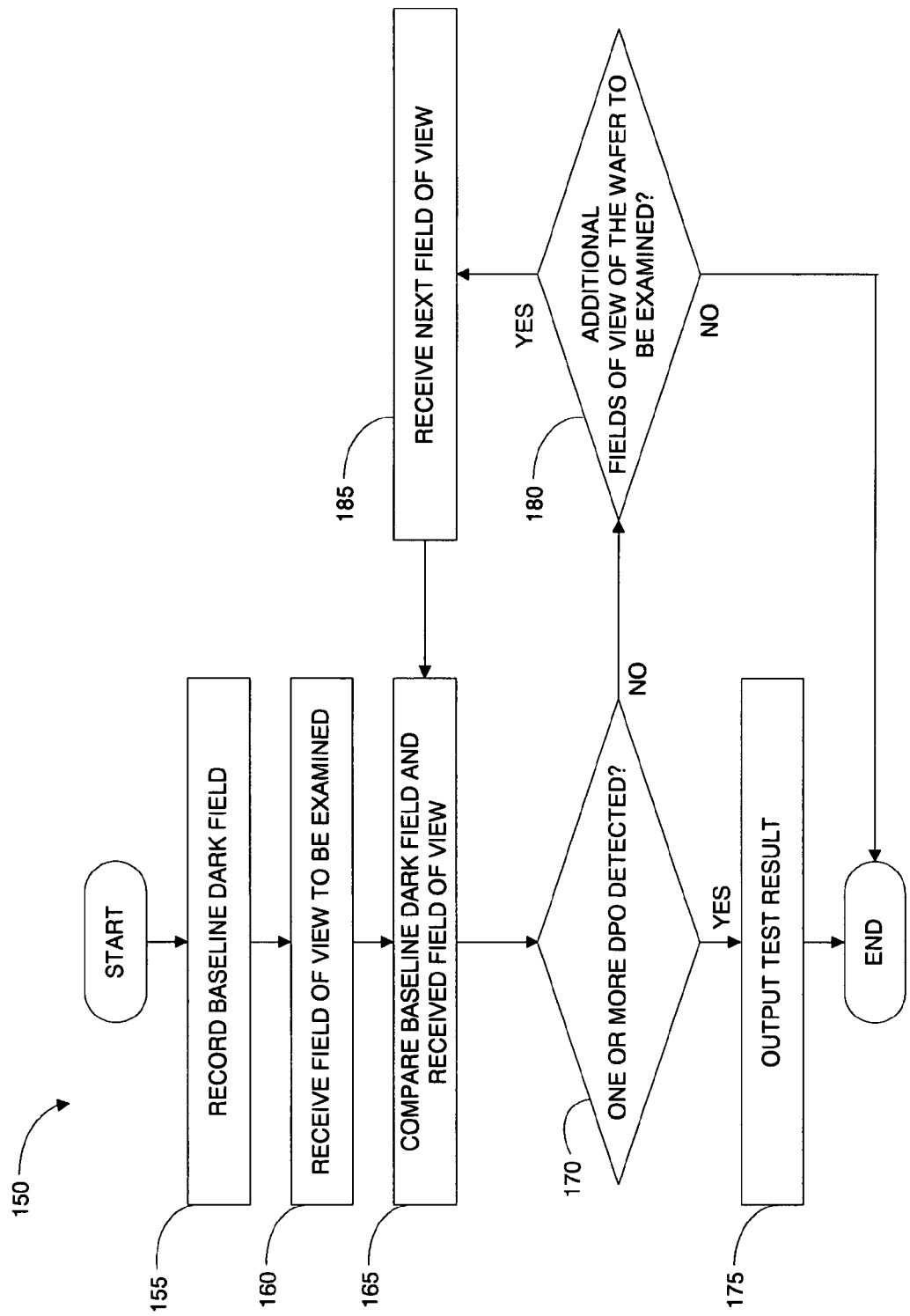
FIG. 1B is a flowchart of the method operations of the in-situ optical inspection system, in accordance with one embodiment of the present invention.

FIG. 1B is a flowchart of the method operations 150 of the in-situ optical inspection system 100, in accordance with one embodiment of the present invention. In an operation 155, a baseline dark field can be recorded. The baseline dark field can be used as a baseline comparison point. By way of example, a field of view of a wafer 108 having no DPOs and therefore substantially zero intensity reflected/diffracted light 112C', 112D' and 112E' is received in the camera 120 can be recorded. The baseline dark field can be used to "filter" very small and therefore very low intensity reflected and/or diffracted light from the surface 108A of the wafer 108. By way of example, some features and devices or combinations of multiple features and devices may cause some low intensity reflected/diffracted light to be received in the camera 120. However, as the devices are supposed to be present, then the devices do not represent DPOs. As a result, the presence of the devices can be filtered out to eliminate false DPO readings. In one embodiment, the presence of the devices can be filtered out by setting a minimum intensity of the reflected/diffracted light 112C', 112D' and 112E' before which the camera 120 will register a presence of a DPO. In one embodiment, the precise location of the devices that cause reflected/diffracted light can be mapped on the surface 108A of the wafer 108. In subsequent operations, any supposed DPOs that are in the locations of the devices can be eliminated as probably being the devices rather than DPOs.

In an operation 160, a field of view to be examined is received in the camera 120. The received field of view can be field of view 122 that includes one or more DPOs can be received in the camera 120.

In an operation 165, the recorded baseline dark field is compared to the received field of view 122, that includes the DPOs 106A, 106B and 106C. As described above, the DPOs 106A, 106B and 106C cause reflected/diffracted light 112C', 112D' and 112E' to be received in the camera 120. The baseline dark field can be compared to the field of view 122 pixel by pixel to identify any pixels that have a respective intensity that is higher than the corresponding pixel in the base line dark field.

In an operation 170, if no DPO is detected in the received field of view then, the wafer 108 passes inspection and the method operations can continue in operation 180. In an operation 180, the wafer is examined to determine if any additional areas or field of views of the surface 108A are yet to be inspected. If no additional field of views are due to be inspected, then the method operations end. Alternatively, if additional fields of view are still remaining to be examined, then in an operation 185, a subsequent field of view is received and the method operations continue in operations 165-170 as described above.

Alternatively, if in operation 170, a DPO is detected in the received field of view, then the inspection process has detected a failure and the detected failure can be indicated a hardware and/or a process failure. If a DPO is detected in operation 170, then the method operations continue in an operation 175. In operation 175, a failure indication is output and the method operations can end. By way of example, a visual or aural alarm can be presented. Alternatively or additionally, any processing of the wafer 108 can immediately cease until an operator is able to intervene.

Figure 2:
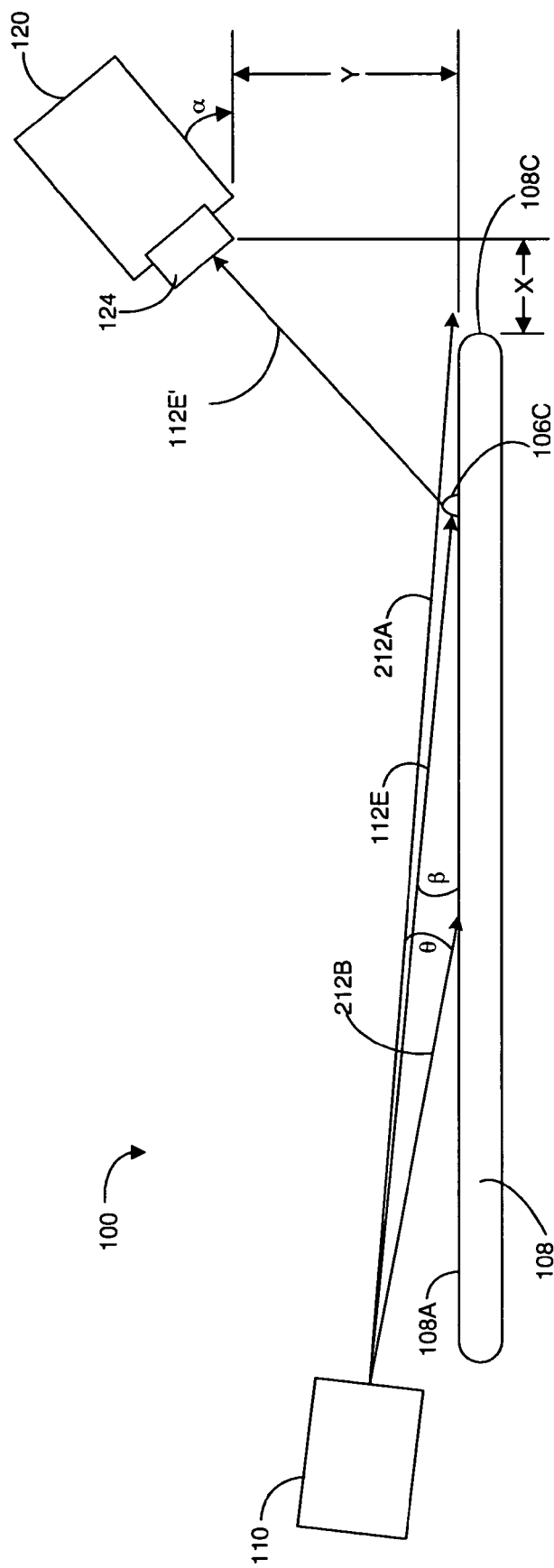
FIG. 2 shows a side view of the in-situ optical inspection system, in accordance with one embodiment of the present invention.

FIG. 2 shows a side view of the in-situ optical inspection system 100, in accordance with one embodiment of the present invention. The light source 110 emits light at an angle β relative to the front surface 108A. Angle β can be with a range of less than about 1 degree to about 180 degrees. Angle β is typically minimized so as to minimize any direct reflection from the surface 108A to the camera 120. Minimizing the direct reflection from the surface 108A to the camera 120 maintains the front surface 108A as a dark field as seen by the camera 120. A dark field as the name implies is a field in which substantially no light is reflected to the camera 120. As the light (e.g., light 112E) impinges on a DPO (e.g., DPO 212A), the light is reflected and/or diffracted into many directions. At least one direction the diffracted light follows is into the camera lens 124 (e.g., light 112E'). As a result, the only object that is highlighted in the dark field is the DPO that reflects and/or diffracts the light.

The light source 110 emits a light in a narrow fan shape defined between edges of the emitted light 212A and 212B. The width of the fan is referred to as the viewing angle θ, as measured between edges of the light 212A and 212B. The viewing angle θ can be with a range of between about 0 degrees to about 90 degrees. By way of example, the viewing angle can be about 8 degrees or about 15 degrees or about 30 degrees.

The angle β of the light source 110 relative to the front surface 108A can be selected so as to cause the edges of the light 212A and 212B to impinge on the surface 108A across a known area. By way of example, the angle β of the light source 110 can be selected so as to cause of the edges of the light 212A, 212B to impinge on the front surface 108A across the entire field of view 122 of the camera 120.

The light source 110 can emit a coherent light (e.g., a laser light) or a single wavelength or a relatively narrow band of wavelengths. The light source 110 can emit visible light or non-visible light (e.g., ultraviolet, infrared, etc.) The wavelength selected to be output from the light source 110 is a function of the wavelengths that the camera 120 can receive and the material and/or type of DPO attempting to detect. By way of example, if a typical DPO is a droplet of water, then a first wavelength of light (e.g., visible light, red light) may be more effective at detecting the droplet of water. Conversely, if the DPO is a droplet of a different chemistry such as an etching chemistry, then a second wavelength of light (e.g., blue, violet or ultraviolet light) may be more effective at detecting the DPO.

The camera 120 can be any type of camera (e.g., a coupled charge device (CCD)) usable for the desired application. By way of example, the camera 120 can be remotely mounted camera that is coupled to the lens 124 by an optical fiber. The camera 120 can be mounted at any angle α suitable for detecting the DPO with a desired field of view 122. The precise angle α is a function of the wavelength of light emitted from the light source 110, the type of DPO to be detected and the desired size of the field of view 122 of the camera 120. By way of example the angle α can be between greater than about 0 degrees and less than about 90 degrees. In one embodiment, the angle α is between about 20 degrees and about 33 degrees.

The camera 120 can also be shifted vertically a distance Y, relative to the front surface 108A of the wafer 108. The camera 120 can also be shifted horizontally a distance X, relative to the edge 108C of the wafer 108. The precise vertical shift Y and horizontal shift X are determined by a function of the space available to move the camera 120 and a desired size of the field of view 122 of the camera 120. By way of example, if the camera 120 has a narrow angle lens 124, then the field of view 122 is correspondingly narrow. As a result, to achieve a field of view 122 wide enough to encompass an entire radius R of the wafer 108, the angle α, the vertical shift Y and horizontal shift X must be selected.

Figure 3:
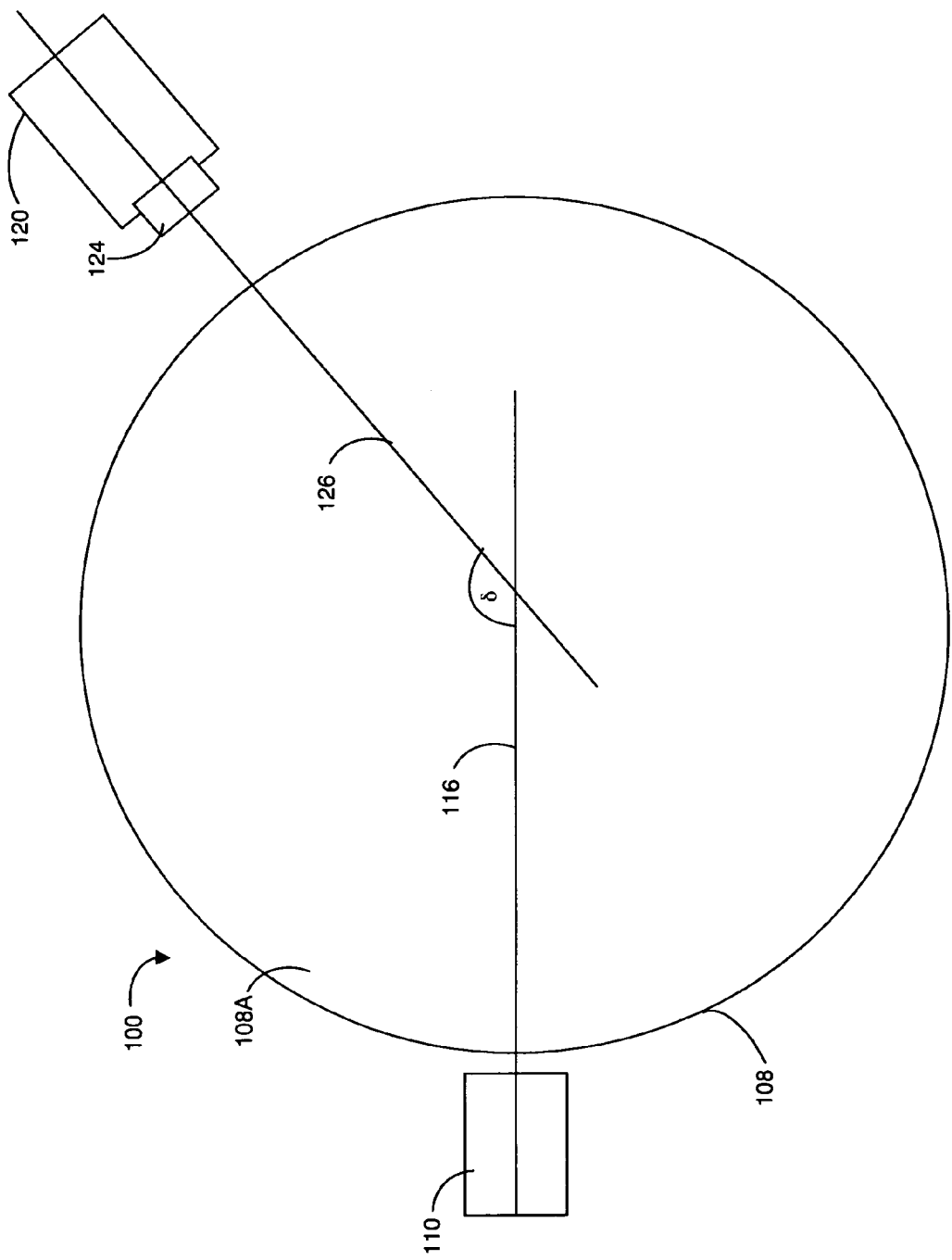
FIG. 3 shows a top view of the in-situ optical inspection system, in accordance with one embodiment of the present invention.

FIG. 3 shows a top view of the in-situ optical inspection system 100, in accordance with one embodiment of the present invention. The top view of the in-situ optical inspection system 100 illustrates the relationship between the centerline 116 of the light source 110 and the centerline 126 of the camera 120. An angle δ is formed between the centerline 116 of the light source 110 and the centerline 126 of the camera 120. The angle δ is typically greater than about 90 degrees and less than about 180 degrees. The precise angle δ, like the angle α described above, is determined by the wavelength of light emitted from the light source 110, the type of DPO to be detected and the desired size of the field of view 122 of the camera 120.

The camera 120 can also be movable such that the field of view 122 can be scanned across the surface 108A of the wafer 108. By way of example one of both of angle α and angle δ can be varied to cause the camera 120 to scan across a portion of the surface 108A of the wafer 108. It may be desirable to scan the camera 120 across the surface 108A if for example the wafer 108 could not be moved relative to the field of view 122 of the camera. Alternatively, if the field of view 122 of the camera 120 were too small, then it may be desirable to scan the camera 120 across the surface 108A so as to allow an optical inspection of the entire surface 108A.

Similarly, the light source 110 may also be movable. By way of example, the light source 110 may be movable to move that area of the surface 108A that is impinged upon by the light 212A, 122E and 212B.

Figure 4:
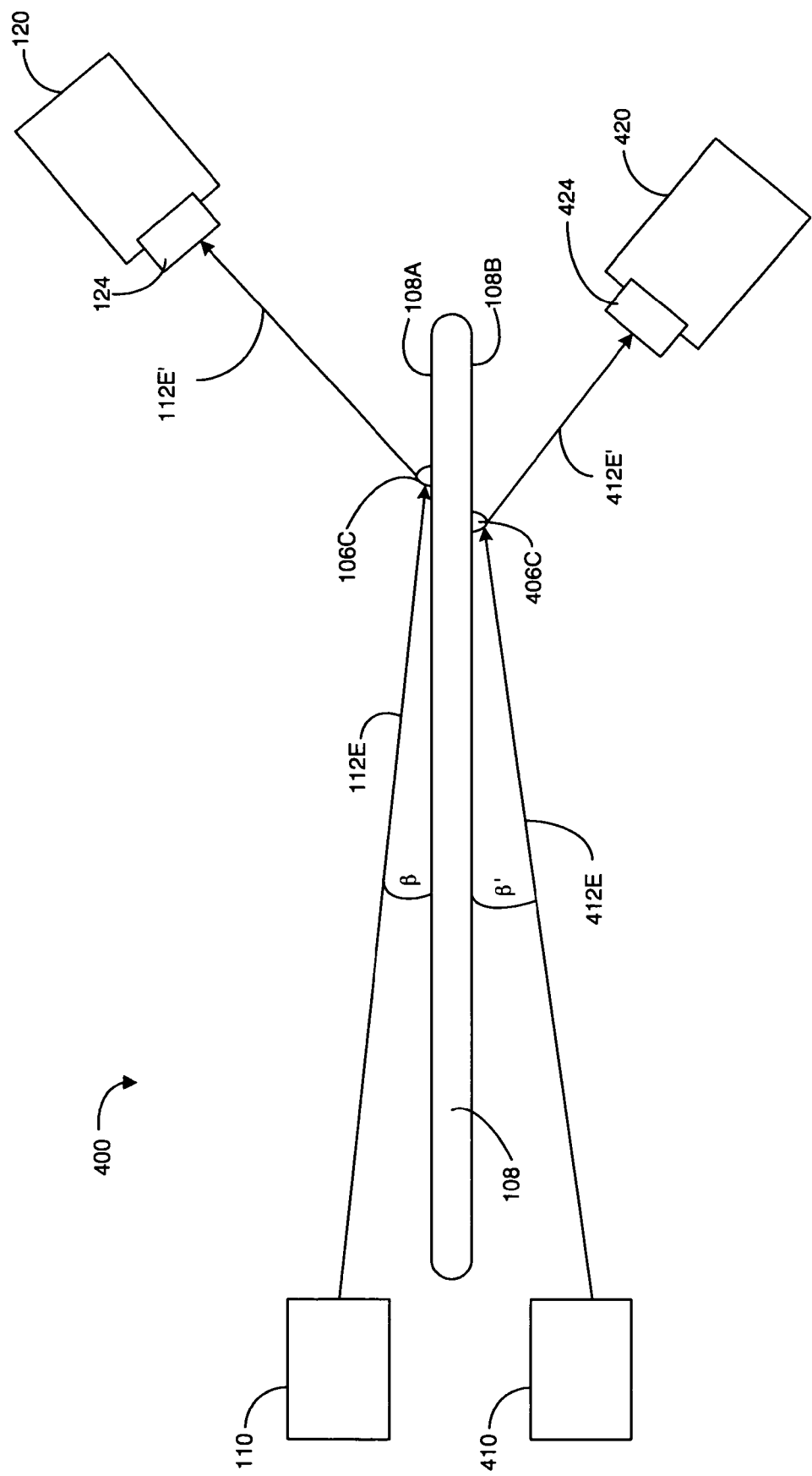
FIG. 4 shows a side view of a dual side, in-situ optical inspection system, in accordance with one embodiment of the present invention.

FIG. 4 shows a side view of a dual side, in-situ optical inspection system 400, in accordance with one embodiment of the present invention. The dual side, in-situ optical inspection system 400 includes the in-situ optical inspection system 100 as described above in FIGS. 1-3 to inspect the front surface 108A of the wafer 108. The dual side, in-situ optical inspection system 400 also includes a second light source 410 and a second camera 420. The second light source 410 emits light 412E that can reflect/diffract from DPO 406C on the back-side surface 108B of the wafer 108. The reflected/diffracted light 412E' is received in the camera 420 through the lens 424.

Figure 5:
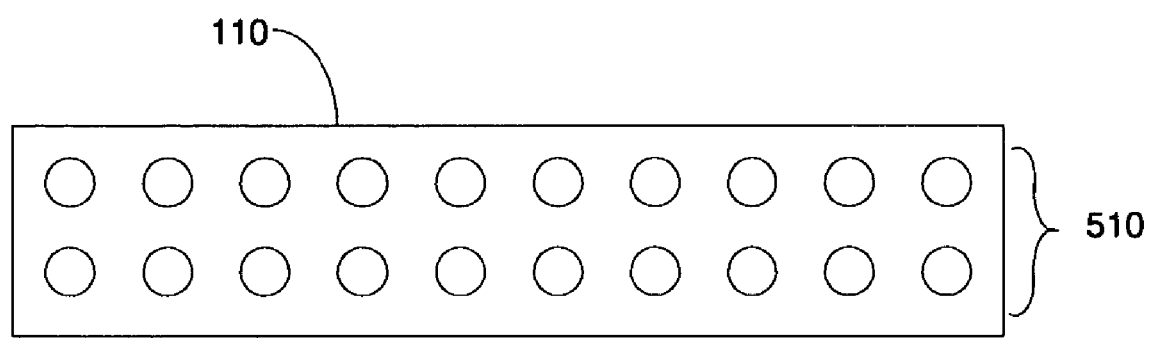
FIG. 5 shows a block diagram of the light source, in accordance with one embodiment of the present invention.

FIG. 5 shows a block diagram of the light source 110, in accordance with one embodiment of the present invention. The light source 110 can include one or more point sources 510 of light. By way of example, each of the point sources 510 of light can be an light emitting diode (LED). Each of the LEDs 510 can emit one or more single wavelengths of light or a band of wavelengths. The intensity and wavelength of the light emitted from the LEDs 510 can be varied so as to better identify any potential DPOs.

Figure 6A:
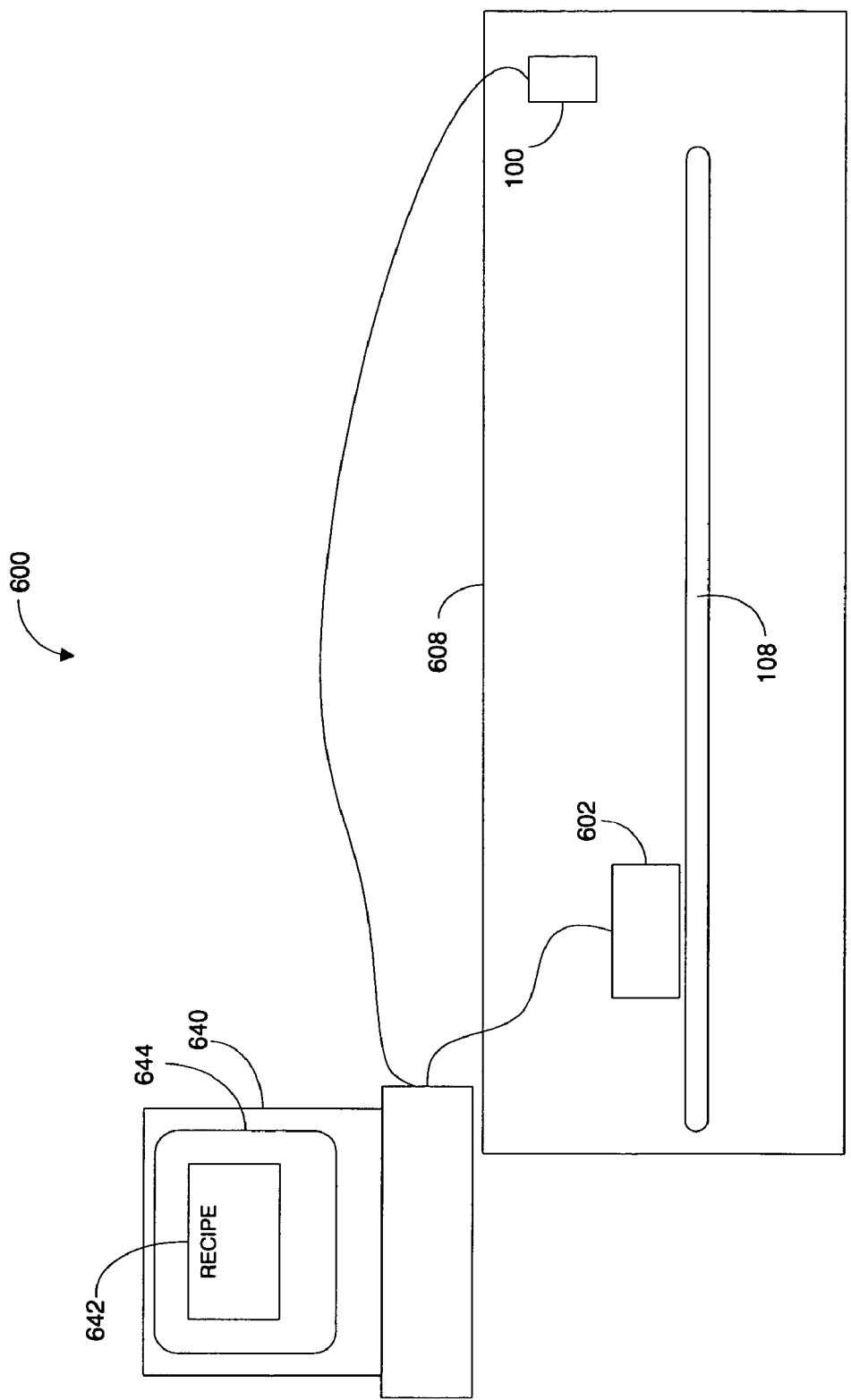
FIGS. 6A and 6B show a proximity head process system, in accordance with one embodiment of the present invention combination.
Figure 6B:
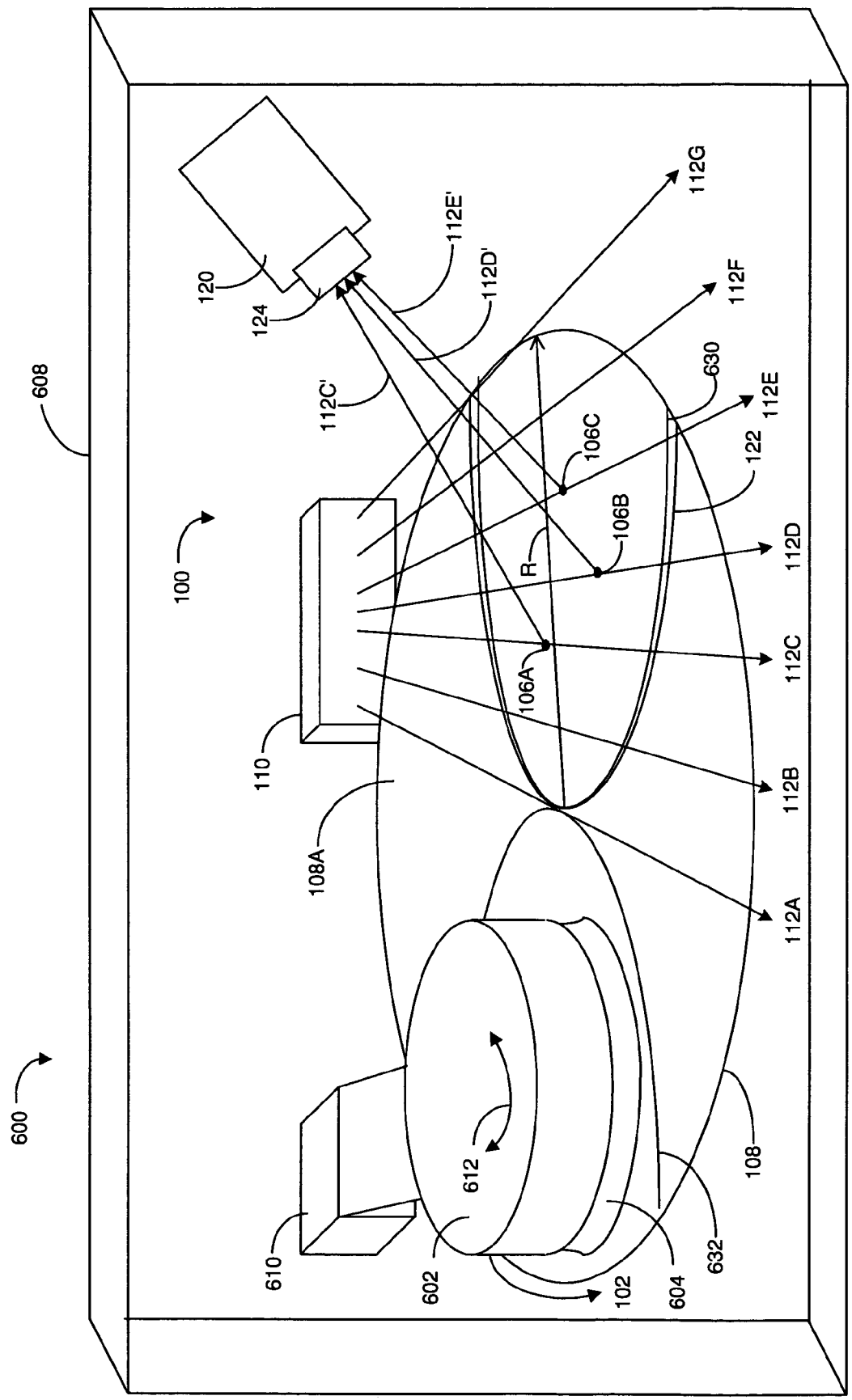

FIGS. 6A and 6B show a proximity head process system 600, in accordance with one embodiment of the present invention combination. FIG. 6A shows the proximity head process system 600 includes a controller 640 and a process chamber 608. The controller 640 can include a visual and/or aural indicator 644 or display that can present a status of the processes occurring within the process chamber 608.

The controller 640 includes a recipe 642 that determines the various operating parameters of the various proximity processes and the inspection processes as described above. By way of example, the recipe 642 determines flowrates of DIW, IPA and IPA vapor and pressures of the vacuum and the precise location of the proximity head 602, the direction and rate of rotation of the wafer 108, if the wafer is rotated, the various angles (i.e., α, δ, β), intensity, wavelength etc. of the in-situ wafer inspection system 100. In one embodiment, the in-situ wafer inspection system 100 can provide feedback to the controller 640. The controller 640 can then modify the recipe 642 in response to the feedback from one or more of the in-situ wafer inspection system 100.

Referring now to FIG. 6B, the process chamber 608 encloses a proximity head 602 and an in-situ wafer inspection system 100 as described above in FIGS. 1-5. The proximity head 602 supports a dynamic liquid meniscus 604 between the proximity head and the surface 108A of the wafer 108. The proximity head 602 can be moved onto and across the surface 108A by an actuator 610. By way of example the actuator or carrier 610 can move the proximity head in either direction 612 across the surface 108A. The dynamic liquid meniscus 604 can apply a process across a portion 630 of the surface 108A of the wafer 108. Moving the wafer 108 and/or the proximity head 602 can move the meniscus 602 across the entire surface 108A and thereby apply the process to substantially all of the surface.

The proximity head 602 can support many different types of processes within the dynamic liquid meniscus 604. By way of example, the dynamic liquid meniscus 604 can support etching, cleaning, rinsing, drying, electroplating, scrubbing, dicing and other processes within the meniscus by selecting various operating parameters, chemistries and incorporating additional mechanisms (e.g., scrubbers, dicing devices, heaters, etc.) within the proximity head 602. Several of the many different types of processes that can be supported by the proximity head 602 and the dynamic liquid meniscus 604 are described in any one or more of the co-owned and co-pending U.S. Patent Applications including: U.S. patent application Ser. No. 10/330,843 filed on Dec. 24, 2002 and entitled "Meniscus, Vacuum, IPA Vapor, Drying Manifold;" U.S. patent application Ser. No. 10/261,839 filed on Sep. 30, 2002 and entitled "Method and Apparatus for Drying Semiconductor Wafer Surfaces Using a Plurality of Inlets and Outlets Held in Close Proximity to the Wafer Surfaces;" U.S. patent application Ser. No. 10/330,897, filed on Dec. 24, 2002, entitled "System for Substrate Processing with Meniscus, Vacuum, IPA vapor, Drying Manifold;" U.S. patent application Ser. No. 10/404,270, filed on Mar. 31, 2003, entitled "Vertical Proximity Processor;" U.S. patent application Ser. No. 10/404,692 filed on Mar. 31, 2003, entitled "Methods and Systems for Processing a Substrate Using a Dynamic Liquid Meniscus;" U.S. patent application Ser. No. 10/606,022, filed on Jun. 24, 2003, entitled, "System and Method for Integrating In-Situ Metrology Within a Wafer Process;" U.S. patent application Ser. No. 10/607,611 filed on Jun. 27, 2003, entitled "Apparatus and Method for Depositing and Planarizing Thin Films on Semiconductor Wafers;" U.S. patent application Ser. No. 10/611,140, filed on Jun. 30, 2003, entitled "Method and Apparatus for Cleaning a Substrate Using Megasonic Power;" U.S. patent application Ser. No. 10/769,498, filed on Jan. 30, 2004, entitled "Stress Free Etch Processing in Combination With a Dynamic Liquid Meniscus;" U.S. patent application Ser. No. 10/742,303, filed on Dec. 18, 2003, entitled "Proximity Brush Unit Apparatus and Method;" U.S. patent application Ser. No. 10/816,432, filed on Mar. 31, 2004, entitled "Substrate Brush Scrubbing and Proximity Cleaning-Drying Sequence Using Compatible Chemistries, and Method, Apparatus, and System for Implementing the Same;" U.S. patent application Ser. No. 10/817,398, filed on Apr. 1, 2004, entitled "Controls of Ambient Environment During Wafer Drying Using Proximity Head;" U.S. patent application Ser. No. 10/817,355, filed on Apr. 1, 2004, entitled "Substrate Proximity Processing Structures and Methods for Using and Making the Same;" U.S. patent application Ser. No. 10/834,548, filed on Apr. 28, 2004, entitled "Apparatus and Method for Providing a Confined Liquid for Immersion Lithography;" U.S. patent application Ser. No. 10/817,620, filed on Apr. 1, 2004, entitled "Substrate Meniscus Interface and Methods for Operation;" U.S. patent application Ser. No. 10/817,133, filed on Apr. 1, 2004, entitled "Proximity Meniscus Manifold;" U.S. patent application Ser. No. 10/883,301, filed on Jun. 30, 2004, entitled "Concentric Proximity Processing Head;" U.S. patent application Ser. No. 10/879,396, filed on Jun. 28, 2004, entitled "Electroplating Head and Method for Operating the Same;" U.S. patent application Ser. No. 10/956,799, filed on Sep. 30, 2004, entitled "Apparatus and Method for Utilizing a Meniscus in Substrate Processing;" and U.S. patent application Ser. No. 10/957,092, filed on Sep. 30, 2004, entitled "System and Method for Modulating Flow Through Multiple Ports in a Proximity Head." The aforementioned patent applications are hereby incorporated by reference in their entirety.

The different configurations described herein generate a dynamic liquid meniscus 604 between the proximity head 602 and the wafer 108. By way of example, the dynamic liquid meniscus 604 may be moved across the wafer 108 to clean and dry the wafer by applying fluid to the surface 108A and removing the fluids from the surface. Therefore, the proximity head 602 can have any numerous types of configurations as shown herein or other configurations that enable the processes described herein. It should also be appreciated that the system 600 may process one surface 108A of the wafer 108 or both the front surface 108A and an opposite, back-side surface 108B of the wafer 108. It should also be appreciated that the fluid used to form and support the dynamic liquid meniscus 604 can be added and withdrawn through the dynamic liquid meniscus so as to constitute a flow through the dynamic liquid meniscus. The fluid flowing through the meniscus can be any suitable type of fluid desired to perform the desired process (e.g., etch, clean, rinse, electroplate, etc.) The dynamic liquid meniscus 604 also dries the surface of the substrate as the dynamic liquid meniscus is drawn away from the surface 108A.

It should be understood that the proximity head 602 may be configured to have at least one of first source inlet configured to input deionized water (DIW) or other process chemistry (also known as a DIW inlet), at least one of a second source inlet configured to input isopropyl alcohol (IPA) in vapor form (also known as IPA inlet), and at least one source outlet configured to output fluids from a region between the wafer and a particular proximity head by applying vacuum (also known as vacuum outlet). It should be appreciated that the vacuum utilized herein may also be suction. In addition, other types of solutions may be inputted into the first source inlet and the second source inlet such as, for example, etching chemistries, photoresist wet stripping chemistries, cleaning solutions, ammonia, HF, etc. It should be appreciated that although IPA vapor is used in some of the exemplary embodiments, other tensio-active substance (substances that provide or increase or decrease a surface tension gradient between a substrate-liquid interface) and nitrogen or other inert carrier gas may be used to carry the tension-active vapor. Alternatives for IPA include but are not limited to the following: diacetone, diaceton alcohol, 1-methoxy-2-propanol, ethylglycol, methyl-pyrrolidon, ethyllactate, 2-butanol. In addition, any other type of vapor or gas may be utilized such as for example, nitrogen, argon or other gases, any suitable alcohol vapor, organic compounds, etc. that may be miscible with water.

In one embodiment, the at least one IPA vapor inlet is adjacent to the at least one vacuum outlet which is in turn adjacent to the at least one DIW inlet to form an IPA-vacuum-DIW orientation. It should be appreciated that other types of orientations such as IPA-DIW-vacuum, DIW-vacuum-IPA, vacuum-IPA-DIW, etc. may be utilized depending on the wafer process that is sought to be enhanced. In a preferable embodiment, the IPA-vacuum-DIW orientation may be utilized to intelligently generate, control, and move the meniscus located between a proximity head and a wafer to clean and dry wafers. The DIW inlets, the IPA vapor inlets, and the vacuum outlets may be arranged in any suitable manner if the above orientation is maintained. For example, in addition to the IPA vapor inlet, the vacuum outlet, and the DIW inlet, in an additional embodiment, there may be additional sets of IPA vapor outlets, DIW inlets and/or vacuum outlets depending on the configuration of the proximity head desired. Therefore, another embodiment may utilize an IPA-vacuum-DIW-DIW-vacuum-IPA or other exemplary embodiments with an IPA source inlet, vacuum source outlet, and DIW source inlet configurations are described herein. It should be appreciated that the exact configuration of the IPA-vacuum-DIW orientation may be varied depending on the application. For example, the distance between the IPA input, vacuum, and DIW input locations may be varied so the distances are consistent or so the distances are inconsistent. In addition, the distances between the IPA input, vacuum, and DIW output may differ in magnitude depending on the size, shape, and configuration of the proximity head 602 and the desired size and shape of a processing meniscus. In addition, the IPA-vacuum-DIW orientation is configured so a vacuum region substantially surrounds a DIW region and the IPA region substantially surrounds at least the trailing edge region of the vacuum region.

Figure 7:
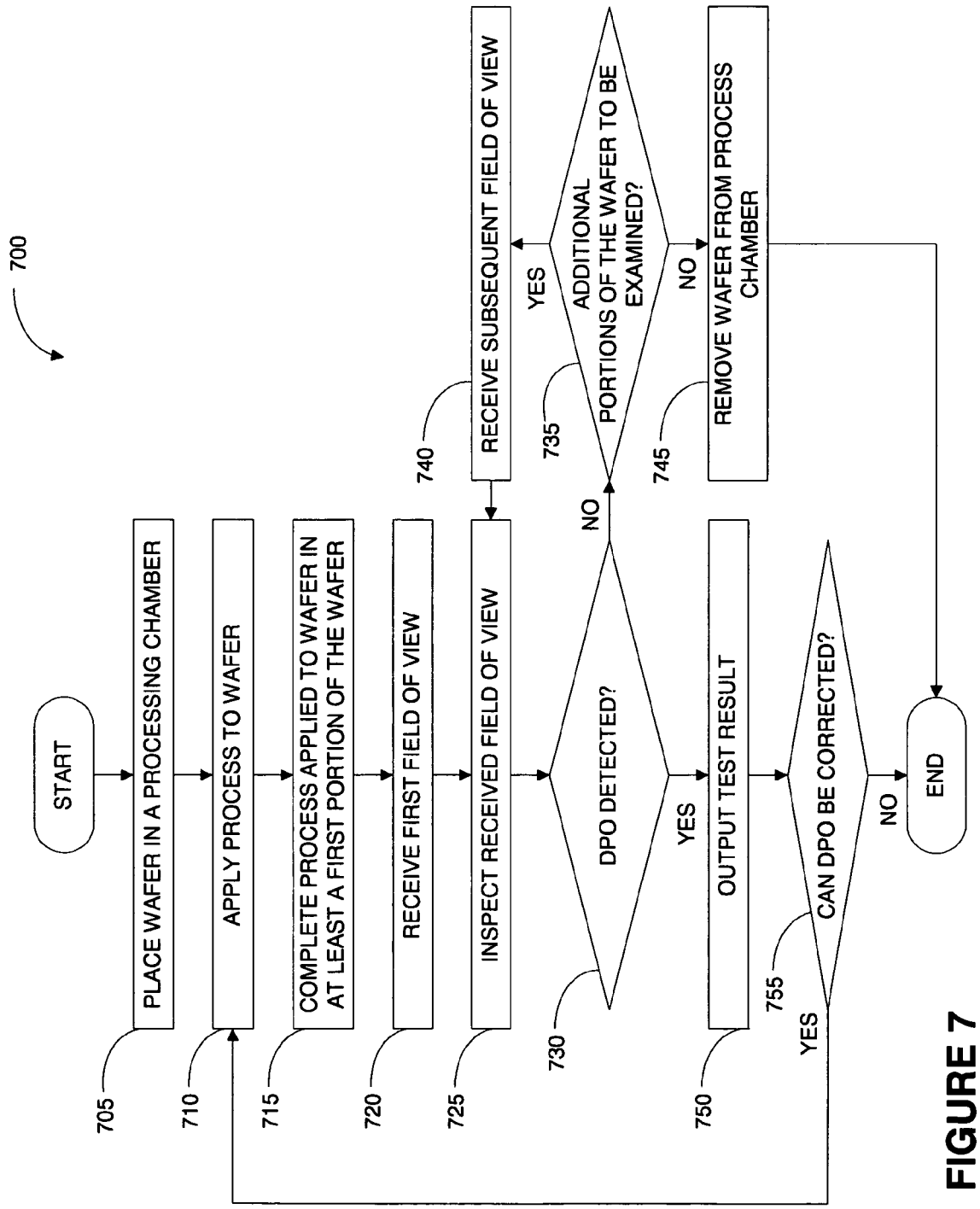
FIG. 7 is a flowchart of the method operation of an in-situ inspection of a wafer using the in-situ optical inspection system, in accordance with one embodiment of the present invention.

FIG. 7 is a flowchart of the method operation 700 of an in-situ inspection of a wafer using the in-situ optical inspection system 100, in accordance with one embodiment of the present invention. In an operation 705, the wafer 108 is placed in a process chamber for processing.

In an operation 710, a process is applied to the wafer 108. By way of example, the process applied to the wafer 108 can include any one or more of an etching process, a cleaning process, a rinsing process, a drying process, an electroplating process, a scrubbing process, a dicing process and other processes, as described above.

In an operation 715, the process applied to the wafer 108 is completed on at least one portion 630 of the front surface 108A of the wafer 108. By way of example, the proximity head 602 can process the first portion 630 of the front surface 108A and move the proximity head to a second portion 632 of the front surface 108A. Moving the proximity head 602 to the second portion 632 of the front surface 108A can include moving the first portion 630 into a field of view of the 122 of the camera 120.

In an operation 720, the first portion 630 of the wafer 108 is inspected using the in-situ optical inspection system 100 and a first field of view is received. In an operation 725, the received field of view is examined as described above.

In an operation 730, the results of the examination are analyzed. If no DPO is detected in operation 730, then the process applied to the wafer 108 in operation 710 above has functioned correctly and in an operation 735, the wafer 108 is examined to determine if additional portions of the wafer are yet to be examined. If additional portions of the wafer 108 are yet to be examined, then in an operation 740 a subsequent field of view of a subsequent portion of the wafer 108 is received and the method operations continue in operation 725 as described above.

If in operation 735, no additional portions of the wafer 108 are yet to be examined, then the method operations continue in operation 745. In operation 745, the wafer 108 can be removed from the process chamber 600. The method operations can then end. A subsequent wafer (not shown) can also be processed in accordance with operations 705 through 730 above.

Alternatively, if in operation 730 a DPO is detected, then the method operations continue in an operation 750. In operation 750, the process applied to the wafer 108 has failed either due to a hardware failure or due to a process error. As a result of the hardware and/or process failure an error signal or indication can be output to an indicator (e.g., on the controller 640). The cause of the DPO (i.e., the hardware and/or process failure) must then be determined before the process can be applied to a subsequent wafer.

If a DPO is detected in operation 730, then in an optional operation 755, the DPO can be examined in to determine if the DPO is of a type that can be corrected by the process applied to the wafer 108 (e.g., in operation 710 above). By way of example, if the process being applied to the wafer 108 is a drying process and the detected DPO is a fluid droplet, then the method operations can continue in operation 710 as described above. In this manner the drying process can be automatically reapplied to the wafer 108.

Alternatively, if the detected DPO is a scratch, chip or pit, and the process applied to the wafer 108 in operation 710 above is not one that can correct the detected DPO, then the method operations end.

While the above embodiments are described in terms of inspecting semiconductor wafers, it should be understood that the same inspection process can be applied to any other type of substrate.

With the above embodiments in mind, it should be understood that the invention may employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations described herein that form part of the invention are useful machine operations. The invention also relates to a device or an apparatus for performing these operations. The apparatus may be specially constructed for the required purposes, or it may be a general-purpose computer selectively activated or configured by a computer program stored in the computer. In particular, various general-purpose machines may be used with computer programs written in accordance with the teachings herein, or it may be more convenient to construct a more specialized apparatus to perform the required operations.

The invention can also be embodied as computer readable code on a computer readable medium. The computer readable medium is any data storage device that can store data which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

It will be further appreciated that the instructions represented by the operations in the above figures are not required to be performed in the order illustrated, and that all the processing represented by the operations may not be necessary to practice the invention. Further, the processes described in any of the above figures can also be implemented in software stored in any one of or combinations of the RAM, the ROM, or the hard disk drive.

Although the foregoing invention has been described in some detail for purposes of clarity of understanding, it will be apparent that certain changes and modifications may be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. A system for inspecting a substrate comprising:
   a camera having a centerline, wherein the centerline is oriented toward a field of view, wherein the field of view encompasses at least a first portion of a first surface of the substrate;
   a light source oriented toward the field of view at a first angle $\beta$ relative to the first surface of the substrate, wherein the first angle $\beta$ orients the light source to emit light impinging the first surface within the field of view, the light source is further oriented at a second angle $\delta$ relative to the centerline, the second angle $\delta$ being between about 90 degrees and less than about 180 degrees, the centerline intersects the first surface at a third angle $\alpha$, the third angle $\alpha$ being between about 20 degrees and about 33 degrees, the first angle $\beta$ is selected to minimize a direct reflection of light from the first portion of the first surface to the camera, wherein the system for inspecting the substrate is included in a process chamber for applying a manufacturing process to the substrate, the manufacturing process being in addition to the inspection process; and
   a controller coupled to the system for inspecting the substrate, wherein the light source includes a plurality of point light sources, wherein each one of the point light sources has a corresponding selected wavelength of light output and wherein the control system includes a logic for selecting one of the plurality of light sources having the selected wavelength of light output and logic for selecting one of a plurality of intensity levels, wherein the selected wavelength of light output and the selected intensity level corresponds to the manufacturing process applied to the substrate.

2. The system of claim 1, wherein the manufacturing process is supported by a dynamic liquid meniscus.

3. The system of claim 2, wherein the dynamic liquid meniscus is supported by a proximity head.

4. The system of claim 1, wherein the light source includes at least one of a group consisting of an light emitting diode (LED) or a laser.

5. The system of claim 1, wherein the light source includes a red LED.

6. The system of claim 1, wherein light source has a first intensity.

7. The system of claim 1, wherein the light source has a viewing angle of less than about 30 degrees.

8. The system of claim 1, wherein the light source has a viewing angle of between about 15 degrees and less than about 8 degrees.

9. The system of claim 1, wherein, the controller includes:
   a recipe; and
   an indicator.

10. A system for inspecting a substrate, comprising:
    a first camera having a first centerline, wherein the first centerline is oriented toward a first field of view, wherein the first field of view encompasses at least a first portion of a first surface of the substrate;
    a first light source oriented toward the first field of view at a first angle $\beta$ relative to the first surface of the substrate wherein the first angle $\beta$ orients the first light source to emit a first light impinging the first surface within the first field of view, the first light source is further oriented at a second angle $\delta$ relative to the first centerline, the second angle $\delta$ being between about 90 degrees and less than about 180 degrees, the first centerline intersects the first surface at a third angle $\alpha$, the third angle $\alpha$ being between about 20 degrees and about 33 degrees;
    a second camera having a second centerline, wherein the second centerline is oriented toward a second field of view, wherein the second field of view encompasses at least a second portion of a second surface of the substrate;
    a second light source oriented toward the second field of view at a fourth angle $\beta'$ relative to the second surface of the substrate, wherein the fourth angle $\beta'$ orients the second light source to emit a second light impinging the second surface within the second field of view, the second light source is further oriented at a fifth angle $\delta'$ relative to the second centerline, the fifth angle $\delta'$ being between about 90 degrees and less than about 180 degrees, the second centerline intersects the first surface at a sixth angle $\alpha'$, the sixth angle $\alpha'$ being between about 20 degrees and about 33 degrees, wherein the first angle $\beta$ is selected to minimize a direct reflection of light from the first portion of the first surface to the first camera, wherein the system for inspecting the substrate is included in a process chamber for applying a manufacturing process to the substrate, the manufacturing process being in addition to the inspection process; and a controller coupled to the system for inspecting the substrate, wherein the light source includes a plurality of point light sources, wherein each one of the point light sources has a corresponding selected wavelength of light output and wherein the control system includes a logic for selecting one of the plurality of light sources having the selected wavelength of light output and logic for selecting one of a plurality of intensity levels, wherein the selected wavelength of light output and the selected intensity level corresponds to the manufacturing process applied to the substrate.

* * * * *